(12) United States Patent
Shi

(10) Patent No.: US 11,684,335 B2
(45) Date of Patent: Jun. 27, 2023

(54) ACOUSTIC TRANSMISSION SYSTEM

(71) Applicant: Georgia Tech Research Corporation, Atlanta, GA (US)

(72) Inventor: Chengzhi Shi, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 64 days.

(21) Appl. No.: 17/092,929

(22) Filed: Nov. 9, 2020

(65) Prior Publication Data

US 2021/0137487 A1 May 13, 2021

Related U.S. Application Data

(60) Provisional application No. 62/932,764, filed on Nov. 8, 2019.

(51) Int. Cl.
*A61B 8/08* (2006.01)
*A61B 8/00* (2006.01)
*B06B 1/02* (2006.01)

(52) U.S. Cl.
CPC .......... *A61B 8/0808* (2013.01); *A61B 8/4281* (2013.01); *A61B 8/4483* (2013.01); *B06B 1/0253* (2013.01); *A61B 8/5207* (2013.01); *B06B 2201/55* (2013.01); *B06B 2201/76* (2013.01)

(58) Field of Classification Search
CPC ... A61B 8/0808; A61B 8/4281; A61B 8/4483; A61B 8/5207; A61B 8/485; A61B 8/5223; A61B 8/0816; A61B 8/0858; A61B 8/0875; A61B 8/085; B06B 1/0253; B06B 2201/55; B06B 2201/76; B06B 1/0246; B06B 1/067
See application file for complete search history.

(56) References Cited

U.S. PATENT DOCUMENTS

2009/0209858 A1* 8/2009 Oelze ................. A61B 8/587
600/443

FOREIGN PATENT DOCUMENTS

WO WO-2018227088 A1 * 12/2018 ........... A61B 5/0035

OTHER PUBLICATIONS

Shen C. et al. "Anisotropic complementary acoustic metamaterial for canceling out aberrating layers." Physical Review X 4.4 (2014): 041033 (Year: 2014).*
Achilleos V. et al. "Non-Hermitian acoustic metamaterials: Role of exceptional points in sound absorption." Physical Review B 95.14 (2017): 144303 (Year: 2017).*

(Continued)

*Primary Examiner* — Christopher Koharski
*Assistant Examiner* — James F McDonald
(74) *Attorney, Agent, or Firm* — Troutman Pepper Hamilton Sanders LLP; Ryan A. Schneider; Nicholas Doss

(57) ABSTRACT

Disclosed herein are acoustic transmission systems comprising an acoustic wave generator configured to generate an acoustic wave and propagate the acoustic wave through a tissue of a specimen, and a non-Hermitian complementary metamaterial (NHCMM) configured to add a first amount of energy amplification coherently to the acoustic wave to account for energy loss in the acoustic wave as a result of the wave propagating through the tissue of the specimen. The acoustic wave generator can be an ultrasound generator, and the tissue can be a cranium.

18 Claims, 16 Drawing Sheets

(56) References Cited

OTHER PUBLICATIONS

Ge, H. et al. Breaking the barriers: advances in acoustic functional materials, National Science Review, (2018) vol. 5, Iss 2, 159-182 (Year: 2018).*

Thevamaran, R., Branscomb, R. M., Makri, E., Anzel, P., Christodoulides, D., Kottos, T., & Thomas, E. L. Asymmetric acoustic energy transport in non-Hermitian metamaterials. Jul. 31, 2019 the Journal of the Acoustical Society of America, 146(1), 863-872. (Year: 2019).*

Zhu, Y. F., Zhu, X. F., Fan, X. D., Liang, B., Zou, X. Y., Yang, J., & Cheng, J. C. (2016). Non-Hermitian acoustic metamaterial for the complete control of sound by accessing the exceptional points. arXiv preprint arXiv:1605.04765. (Year: 2016).*

* cited by examiner

ACOUSTIC TRANSMISSION SYSTEM

CROSS-REFERENCE TO RELATED APPLICATIONS

This application claims the benefit of U.S. Provisional Application Ser. No. 62/932,764, filed on 8 Nov. 2019 the entire contents and substance of which is incorporated herein by reference in its entirety as if fully set forth below.

FIELD OF THE DISCLOSURE

The present disclosure relates generally to acoustic transmission systems and methods. Particularly, embodiments of the present disclosure relate to systems and methods for acoustic transmission systems and methods for propagating through tissue.

BACKGROUND

Acoustic waves are widely used in biomedical applications because of their biocompatibility and penetration depth through tissue. In particular, high frequency ultrasound can be applied safely for imaging and medical diagnosis for decades. Ultrasound is considered one of the most biocompatible imaging modalities as it requires no ionizing radiation, penetrates deep into biological tissues, and offers superior resolution compared to other imaging techniques. Recently, developments at the focal point of focused ultrasound has increased the usefulness of ultrasound in the development of noninvasive treatments for different diseases, such as lithotripsy for kidney stones, ablation and histotripsy for tumors and thrombosis, thalamotomy for tremors, and drug delivery through the blood-brain barrier. Even with these significant impacts on biomedical imaging and therapies, ultrasound has fallen short in many applications.

Although high frequency ultrasound increases the precision and spatial resolution of the aforementioned biomedical applications, major challenges exist to adapt these techniques for lossy mediums and tissue, such as skull/brain imaging and brain therapies. The primary problem with such therapies is the property of the skull to act as a highly mismatched impedance barrier with strong attenuative effects. This lossy acoustic barrier drastically limits the transmission of ultrasound energy, and other similar acoustic waves, into the brain, inhibits the effectiveness of high frequency ultrasound, and prevents diagnostic imaging capabilities.

What is needed, therefore, are acoustic imaging systems that can overcome biological, mismatched, and lossy acoustic barriers, such as the cranium. Embodiments of the present disclosure address this need as well as other needs that will become apparent upon reading the description below in conjunction with the drawings.

BRIEF SUMMARY OF THE DISCLOSURE

The present disclosure relates generally to acoustic transmission systems and methods. Particularly, embodiments of the present disclosure relate to systems and methods for acoustic transmission systems and methods for propagating through tissue.

An exemplary embodiment of the present disclosure can provide an acoustic transmission system comprising: an acoustic wave generator configured to generate an acoustic wave and propagate the acoustic wave through a tissue of a specimen; and a non-Hermitian complementary metamaterial (NHCMM) configured to add a first amount of energy amplification coherently to the acoustic wave to account for energy loss in the acoustic wave as a result of the wave propagating through the tissue of the specimen.

In any of the embodiments disclosed herein, the NHCMM can have a first bulk modulus and a first density having an opposite sign to a second bulk modulus and a second density of the tissue, respectively.

In any of the embodiments disclosed herein, the tissue can be a cranium.

In any of the embodiments disclosed herein, the first amount of energy amplification added coherently to the acoustic wave by the NHCMM can compensate for an energy loss in the acoustic wave as a result of the acoustic wave propagating through the cranium.

In any of the embodiments disclosed herein, the acoustic wave generator can be an ultrasound generator.

In any of the embodiments disclosed herein, the system can further comprise: a transducer; a processor; and a memory storing instructions that, when executed by the processor, cause the system to: transmit a first acoustic wave from the acoustic wave generator through the tissue to determine the second bulk modulus and the second density; calculate an impedance mismatch and an intrinsic loss of the tissue; alter the NHCMM to coherently amplify the first amount of energy to compensate for the impedance mismatch and the intrinsic loss; and transmit a second acoustic wave from the acoustic wave generator through the tissue.

In any of the embodiments disclosed herein, the instructions can further cause the system to: measure a pressure field of the tissue with the transducer; calculate a contrast to noise ratio of the pressure field; and determine that an anomaly is present in the pressure field by comparing a higher amplitude backscattered pressure field to the pressure field.

In any of the embodiments disclosed herein, the NHCMM can comprise a resonating structure.

In any of the embodiments disclosed herein, the NHCMM can be positioned proximal to the tissue.

Another embodiment of the present disclosure can provide a method of acoustic wave transmission, the method comprising: transmitting a first acoustic wave from an acoustic wave generator to propagate the first acoustic wave through a tissue of a specimen to determine a first bulk modulus and a first density of the tissue; calculating an impedance mismatch and an intrinsic loss of the tissue; altering a non-Hermitian complementary metamaterial (NHCMM) to have a second bulk modulus and a second density having an opposite sign to the first bulk modulus and the first density and configured to add a first amount of energy to the first acoustic wave to compensate the impedance mismatch and the intrinsic loss to form a second acoustic wave; and transmitting the second acoustic wave from the acoustic wave generator into the tissue, wherein the NHCMM is positioned proximal to the tissue.

In any of the embodiments disclosed herein, the method can further comprise: measuring a pressure field produced by the second acoustic wave propagating through the tissue by the transducer; calculating the contrast to noise ratio of the pressure field; and determining that an anomaly is present in the pressure field by comparing a higher amplitude backscattered pressure field to the pressure field.

Another embodiment of the present disclosure can provide an acoustic transmission system comprising: a transducer; a processor; and a memory storing instructions that, when executed by the processor, cause the system to:

transmit a first acoustic wave from an acoustic wave generator to propagate the first acoustic wave through a tissue of a specimen to determine a first bulk modulus and a first density of the tissue; calculate an energy loss in the first acoustic wave as a result of the first acoustic wave propagating through the tissue; alter a non-Hermitian complementary metamaterial (NHCMM) to coherently amplify a first amount of energy to the acoustic wave generator to compensate the energy loss in the first acoustic wave to form a second acoustic wave; and transmit the second acoustic wave from the acoustic wave generator into the tissue, wherein the NHCMM is positioned proximal to and the tissue.

In any of the embodiments disclosed herein, the instructions can further cause the system to: measure a pressure field produced by the second acoustic wave propagating through the tissue by the transducer; calculate the contrast to noise ratio of the pressure field; and determine that an anomaly is present in the pressure field by comparing a higher amplitude backscattered pressure field to the pressure field.

In any of the embodiments disclosed herein, the tissue can be a cranium.

In any of the embodiments disclosed herein, the acoustic wave generator can be an ultrasound generator.

In any of the embodiments disclosed herein, the NHCMM can comprise a resonating structure.

In any of the embodiments disclosed herein, the NHCMM can be in electrical communication with an electronic circuit.

In any of the embodiments disclosed herein, the electronic circuit can comprise piezoelectric materials connected to an amplification and a phase control circuit.

These and other aspects of the present disclosure are described in the Detailed Description below and the accompanying figures. Other aspects and features of embodiments of the present disclosure will become apparent to those of ordinary skill in the art upon reviewing the following description of specific, exemplary embodiments of the present invention in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION

Figure 1:
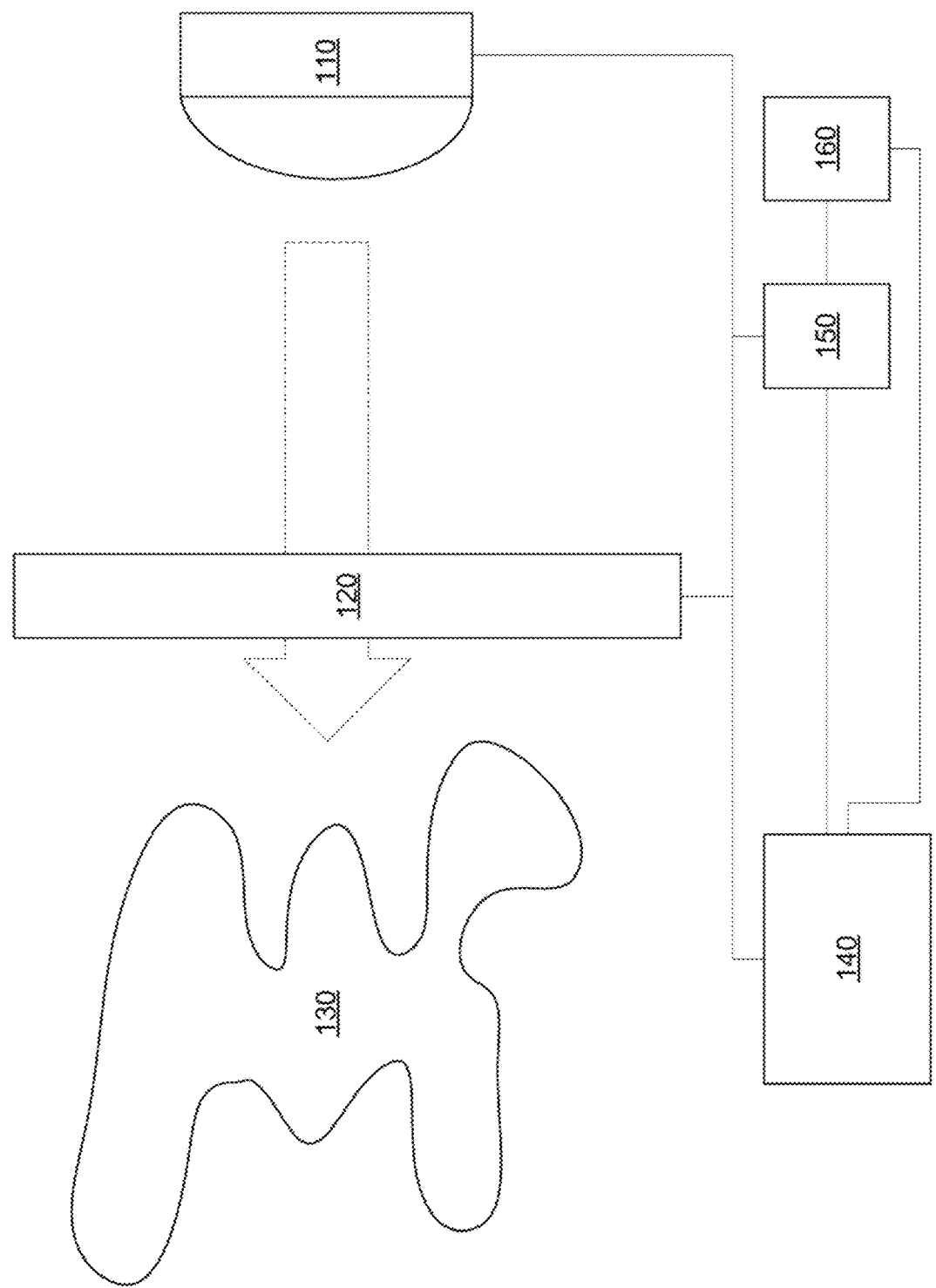
FIG. 1 illustrates a diagram of an acoustic transmission system according to some examples of the present disclosure.

To mitigate the scattering and loss caused by the skull, acoustic metamaterials can utilize transformation acoustics to enable bidirectional acoustic transmission into the brain, paving the way to non-invasive diagnostic brain imaging and non-invasive brain therapies. Complementary metamaterials (CMM) can be designed with the negative real acoustic properties of the aforementioned acoustic barrier to effectively counteract any impedance mismatch effects to transmit through lossless impedance barriers. However, CMMs can be ineffective for acoustic transmission through the skull, as the porosity of cranial bone creates a lossy interior structure. As a result, the purely real-valued sound speed and density will not fully characterize the acoustic impedance, resulting in an impedance mismatch when using a CMM on a lossy barrier. In addition, the CMM does not contain an effective acoustic gain that can compensate for the intrinsic loss of the skull. To overcome the loss of the skull and achieve total acoustic transmission, non-Hermitian complementary metamaterials (NHCMM) can be designed with an active energy input to directly counteract the loss of the skull. Since the NHCMM considers both the real and imaginary material parameters of the lossy barrier, the bilayer can act as an invisible media to ultrasound, allowing bidirectional acoustic transmission.

Disclosed herein are acoustic transmission systems taking advantage of the use of NHCMMs for ultrasonic imaging by considering several bone irregularities typical to the skull, such as changes in curvature, thickness, and the presence of cavities in the skull. The NHCMM can be adaptable to ensure lossless transmission through any skull, or other tissue, geometry for practical use of NHCMMs. Also disclosed herein is a multilayer system consisting of the NHCMM, tissue (e.g., a skull and brain tissue), and a tumor structure, with physiologically accurate geometries and material parameters.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

As used herein, the terms "tissue" and "specimen" can refer to any plurality of biological cells, living or dead, and/or any number of other biomaterials, including, but not limited to, any single instance or plurality of bones, organs, muscles, and the like.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

FIG. 1 illustrates an acoustic transmission system 100. The system 100 can comprise an acoustic wave generator 110 and a non-Hermitian complementary metamaterial (NHCMM) 120. The acoustic wave generator 110 can be configured to generate an acoustic wave and propagate the acoustic wave through the tissue of a specimen 130. The NHCMM 120 can be configured to coherently amplify the amount of energy in the acoustic wave to account for energy loss in the acoustic wave as a result of the wave propagating through the tissue 130.

The NHCMM 120 can be configured to have a bulk modulus and a density of an opposite sign (e.g., negative or positive) to the bulk modulus and the density of the tissue 130. In such a manner, the impedance mismatch of the tissue 130 can be offset to reduce the reflection of the acoustic waves transmitted by the acoustic wave generator. The NHCMM 120 can therefore be positioned proximal to the tissue 130 to ensure that the NHCMM 120 can interact with the acoustic waves upon the acoustic waves interacting with the tissue 130.

The aim of the system 100 is to obtain the desired values of the NHCMM material parameters that can enable near perfect transmission and wavefront restoration when the acoustic wave (e.g., high frequency ultrasound) propagates through the combined layers of NHCMM 120 and the tissue 130. To achieve this, a simplified model consisting of the NHCMM 120 and the tissue 130 adjacent to each other can be used, as shown in FIG. 1. The top part of the tissue 130 can be assumed to be submerged in water; therefore, the background medium outside the tissue 130 can be modeled as water. If the tissue 130 is, for example, a brain, the brain can also be modeled as water due to having similar physical properties. A simplified model of the transmission layers in FIG. 1 are illustrated in FIG. 2.

Figure 2:
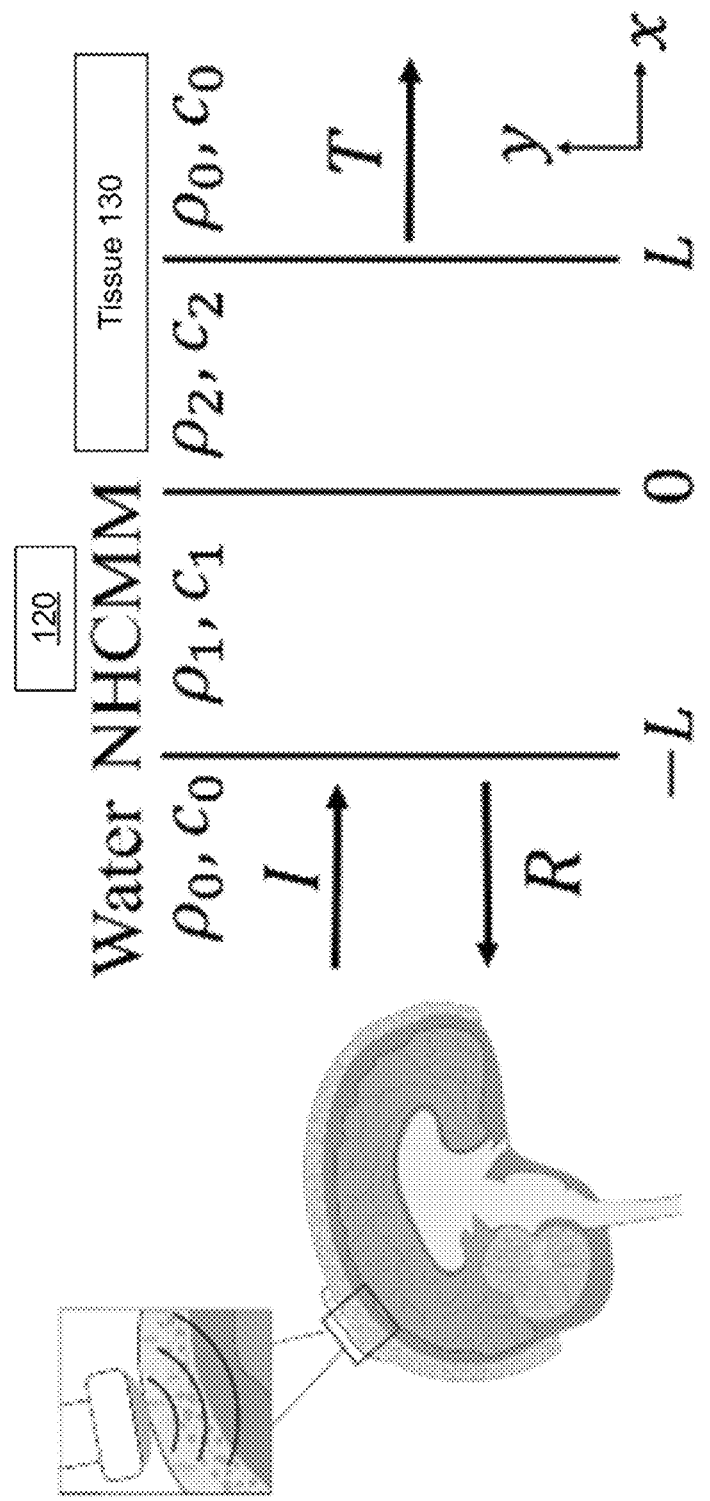
FIG. 2 illustrates another diagram of an acoustic transmission system according to some examples of the present disclosure.

As shown in FIG. 2, by applying continuity boundary conditions at the each of the boundaries, it can be observed that a solution given by $\rho_t = -\rho_2$ and $c_1 = -c_2$ gives a total transmission (T=1) and no reflection (R=0). Variables p and c are the density and sound speed of longitudinal waves, and the subscripts 1 and 2 denote the NHCMM 120 and the tissue 130, respectively. It can be appreciated that $\rho_2$ and $c_2$ can be complex-valued because of the intrinsic loss properties of the tissue 130. Therefore, $\rho_1$ and $c_1$ can be the direct opposite complex-valued material parameters of the tissue 130.

Physically, this opposite density and sound speed can result in an identical acoustic impedance and an opposite refractive index of the NHCMM 120 when compared with the tissue 130. These material parameters can suppress the impedance mismatch of the barrier of the tissue 130 while the opposite imaginary parts indicate that the NHCMM 120 can contain active gain materials that can compensate the wave attenuation through the lossy tissue layers.

The NHCMM 120 can be configured to have a resonating structure and piezoelectric materials. As would be appreciated, the properties of the resonating structure can enhance the signal at the working acoustic (e.g., ultrasound) frequency to enhance the signal to noise ratio for better imaging quality and/or therapy performance. The resonating structure can be, for instance, an acoustic resonator or an electrical circuit resonating with the piezoelectric materials. Such components can also be connected to an electronic circuit, which is in turn connected to the NHCMM 120 itself. The electronic circuit can be an amplification and a phase control circuit. The negative real parts of the NHCMM 120 material parameters can be realized by the resonating structures, while the imaginary parts can be contributed by active gain elements. The active gain elements can be achieved by adding piezoelectric materials connected with amplification circuits used in the realization of parity-time (PT) symmetric acoustics, nonreciprocal propagation, and time reversal signal processing.

While total transmission can be realized at the exceptional points of PT symmetric acoustics where active gain units were used, the physics of the NHCMM 120 and PT symmetric acoustics can be completely different. PT symmetry requires the material parameters to satisfy satisfy $\rho_1 = \rho_2^*$ and $c_1 = c_2^*$, where the superscript * denotes the complex conjugate of the corresponding parameter, which does not hold for the NHCMM 120. In physics, the total transmission and zero reflection can be true for waves incident from both sides of the bilayer structure, making the whole system 100 energy conservative.

Referring back to FIG. 1, the system 100 can also comprise a transducer 140, a processor 150, and a memory 160. The transducer 140, the processor 150, and the memory 160 can be in communication with one another as well as in communication with the acoustic wave generator 110 and the NHCMM 120. The various components of the system 100 can communicate to enact some or all of the methods described below.

Figure 3:
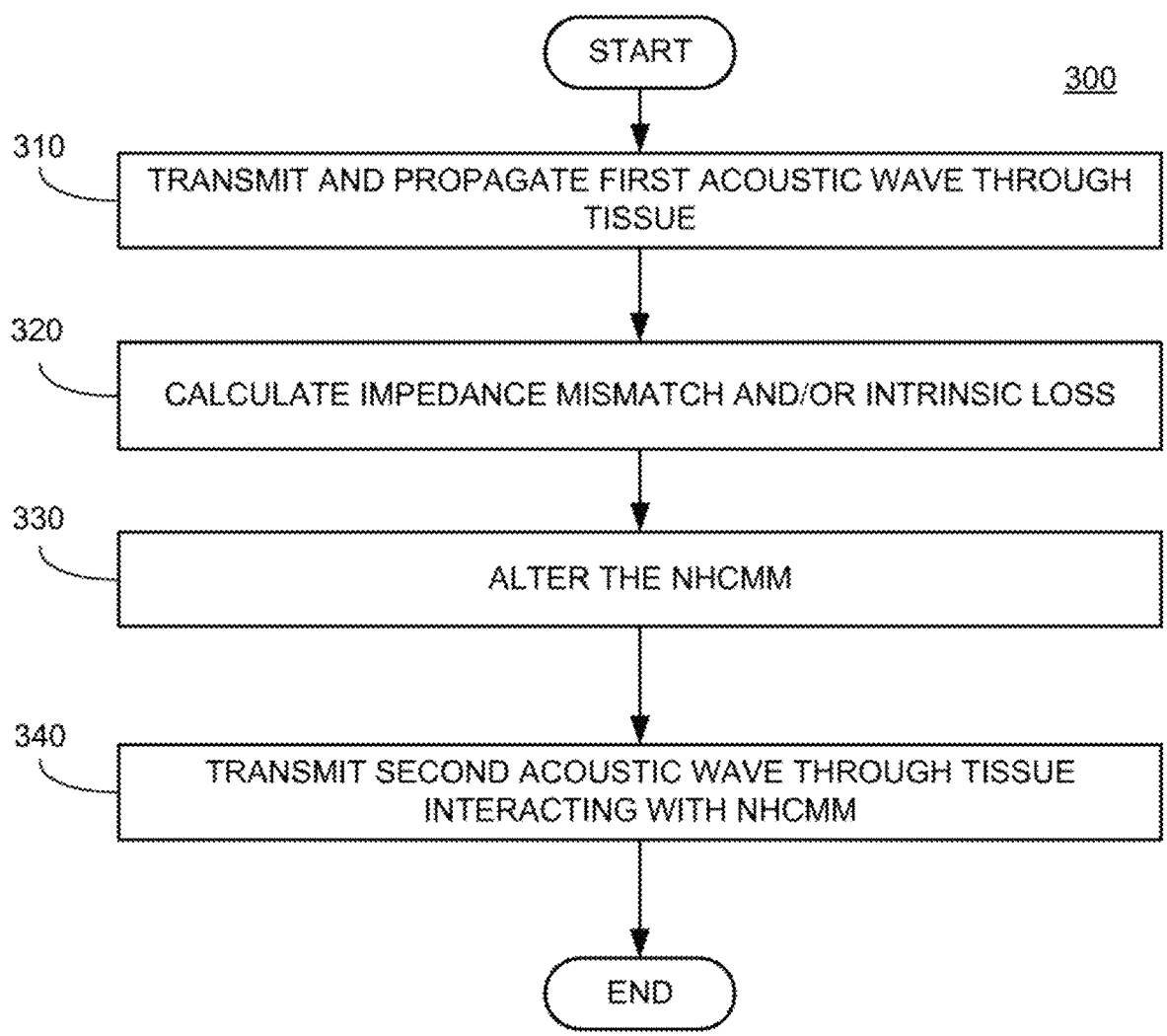
FIG. 3 illustrates a flowchart of a method of acoustic transmission according to some examples of the present disclosure.

FIG. 3 illustrates a flowchart of an example method 300 of acoustic wave transmission. While the method 300 is described with respect to the system 100, it is understood that some or all of the method 300 can be implemented using other similar systems, computing devices, general purpose computers, and the like.

As shown, in block 310, the acoustic wave generator 110 can transmit and propagate a first acoustic wave through the tissue 130 to determine the bulk modulus and the density of the tissue 130. The acoustic wave generator 110 can be, for example, an ultrasound generator. The tissue 130 can be, for example, a cranium or a brain. The acoustic wave generator 110 can work in tandem with the transducer 140 to measure a pressure field produced by the acoustic wave propagating through the tissue 130. The method 300 can then proceed on to block 320.

In block 320, the processor 150 can calculate an impedance mismatch and an intrinsic loss of the tissue 130. The processor 150 can also calculate an energy loss in the first acoustic wave. Examples of these calculations are given and explained in further detail below. Once these values are calculated, the method 300 can then proceed on to block 330.

In block 330, the system 100 can alter the NHCMM 120. The NHCMM 120 can be altered, for example, to coherently amplify an amount of energy in the transmitted acoustic waves to compensate the calculated energy loss/intrinsic loss and/or the impedance mismatch. This can be performed by changing the resonant structure and/or the piezoelectric properties of the NHCMM 120. The resulting acoustic wave can have sufficient energy after interacting with the NHCMM 120 to overcome the loss resulting from propagation through the tissue 130. Alternatively, or additionally, the NHCMM 120 can also have its density and/or bulk modulus altered to have a sign opposite to the density and the bulk modulus of the tissue 130. The method 300 can then proceed on to block 340.

In block 340, the acoustic wave generator 110 can transmit another acoustic wave into the tissue 130. This second acoustic wave can interact with the NHCMM 120 prior to propagating through the tissue 130. In such an example, the NHCMM 120 can be positioned proximal to the tissue 130. The transducer 140 can continue to monitor the pressure field produced as a result of the acoustic waves propagating through the tissue. The processor 150 can calculate the contrast to noise ratio of the pressure field. The processor 150 and/or the transducer 140 can operate continuously in tandem, or one or both of the aforementioned components can operate batch-wise. In some examples, an anomaly can be detected in the tissue by calculating and comparing a higher amplitude backscattered pressure field to the previously measured pressure field. The method 300 can then terminate after block 340.

Certain embodiments and implementations of the disclosed technology are described above with reference to block and flow diagrams of systems and methods and/or computer program products according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

EXAMPLES

Example 1

Because the system 100 can provide for obtaining the material parameters of the NHCMM for noninvasive ultrasonic brain imaging where high frequency acoustic waves are used, calculations at 1.5 MHz can be used by way of illustration, and not limitation. At this frequency, the measured effective density and sound speed of longitudinal acoustic waves are 1900 kg/m$^3$ and 2835 m/s with an acoustic attenuation of 25 dB through a 4 mm thick human skull sample. These acoustic properties can be closely equivalent to complex-valued material parameters $\rho_2$=(1900+50i) kg/m$^3$ and $c_2$=(2835+80i) m/s in numerical calculations. These values can be obtained based on the loss characterization and parameter retrieval, where i is the imaginary unit. These complexed-valued parameters are therefore used for further calculations for the purposes of illustration, not limitation. From the analytical derivation listed above, the density and sound speed of the NHCMM can be chosen to be $\rho_1$=−0.9999(1900+50i) kg/m$^3$ and $c_1$=−0.9999(2835+80i) m/s to avoid a singularity in the calculations. The density and sound speed of water and brain ($\rho_0$=1000 kg/m$^3$ and $c_0$=1500 m/s) can be used in such numerical calculations. The averaged thickness of a human skull is L=1 cm, which can be used herein. All numerical simulations can be performed in COMSOL Multiphysics 5.3.

Figure 4A:
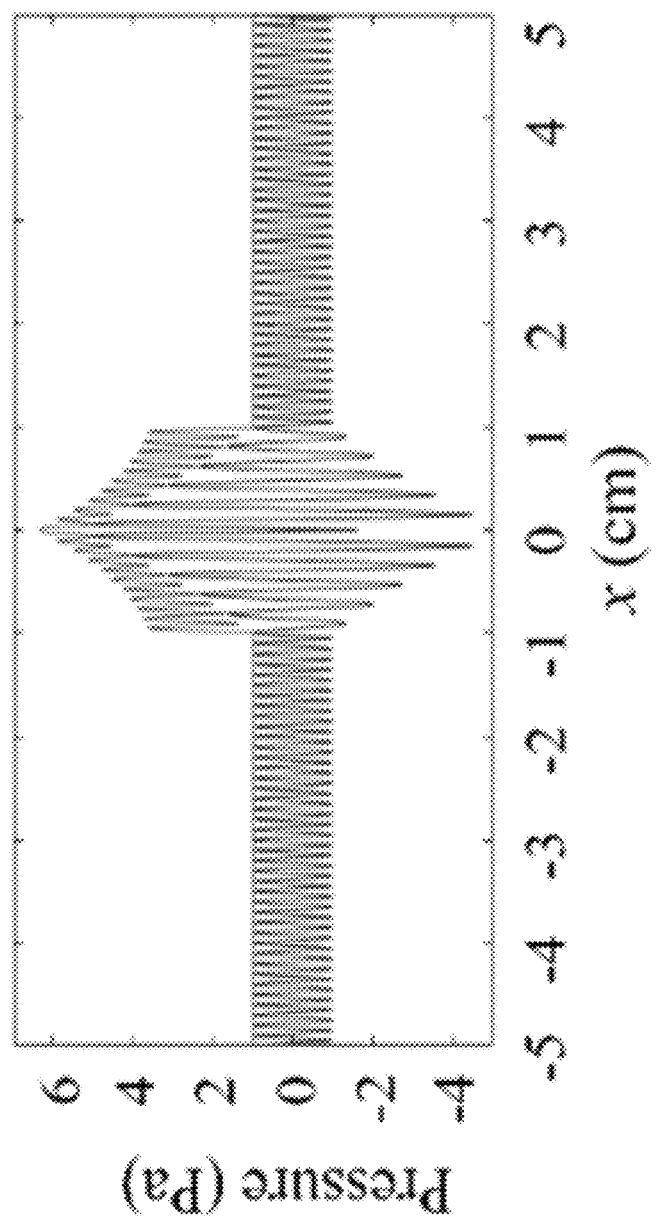
FIGS. 4A-E illustrate acoustic wave compensation through the tissue of a specimen compensated by various materials according to some examples of the present disclosure.
Figure 4B:
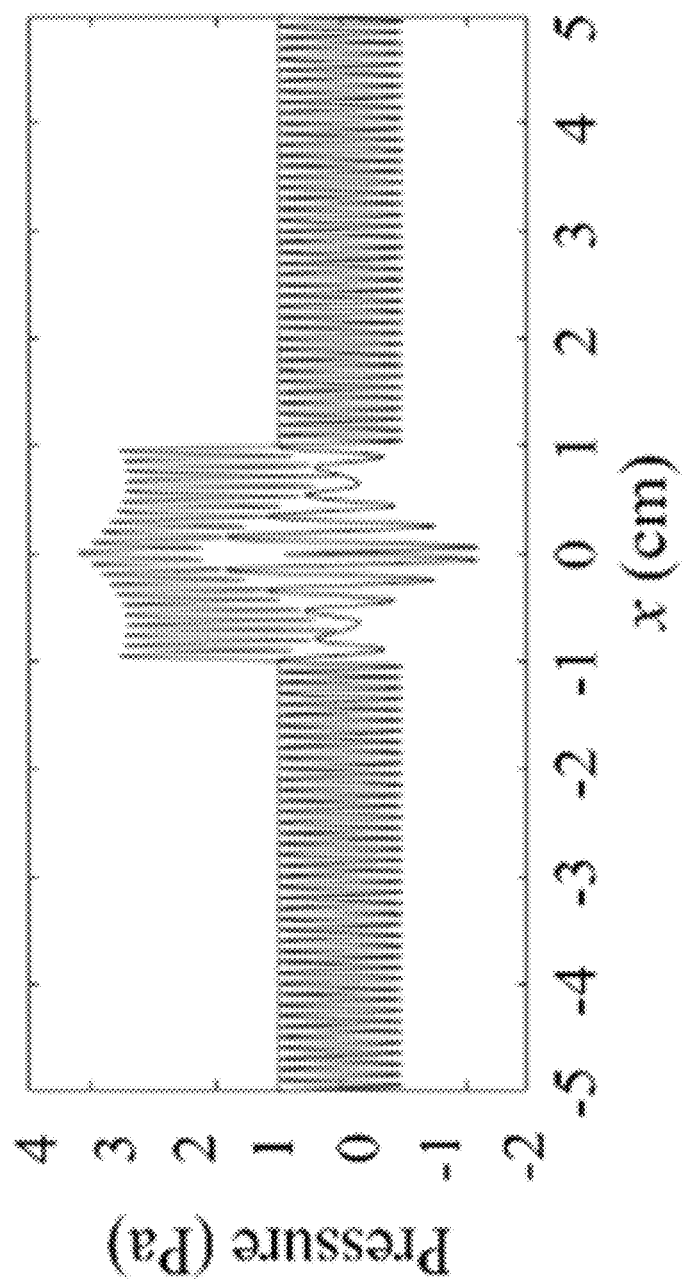

To analyze the transmission and reflection properties of the combined NHCMM and skull layer, an acoustic plane wave can be modeled propagating through the bilayer structure from both incident sides (FIGS. 4A and 4B). The origin of the coordinate can be set at the boundary between the NHCMM and skull, which are both 1 cm thick. For both cases, the transmission can be 100% with no reflection, demonstrating the suppression of the loss skull barrier induced by the NHCMM. The sound speeds through the NHCMM and the skull are of equal magnitude but opposite sign resulting an effective zero refractive index, and hence no phase accumulation occurs through the structure. The interference patterns in the bilayer indicate multiple reflections in between the boundaries. Thus, the energy damped by the lossy skull barrier can be balanced by the gain of the NHCMM. For both incident cases, the highest acoustic amplitude can occur at the boundary between the NHCMM and skull. For steady state, the peak acoustic amplitude can reach its highest value when the wave is incident from the water side due to the gain NHCMM amplifying the signal to a higher energy level before being damped by the lossy skull layer. In the opposite case, the wave can be damped to a lower energy level in the skull layer before entering the gain medium incident from the brain side. Therefore, the energy needed to compensate the skull loss from the active gain element of the NHCMM can be smaller when the wave is scattered back from the brain.

Figure 4C:
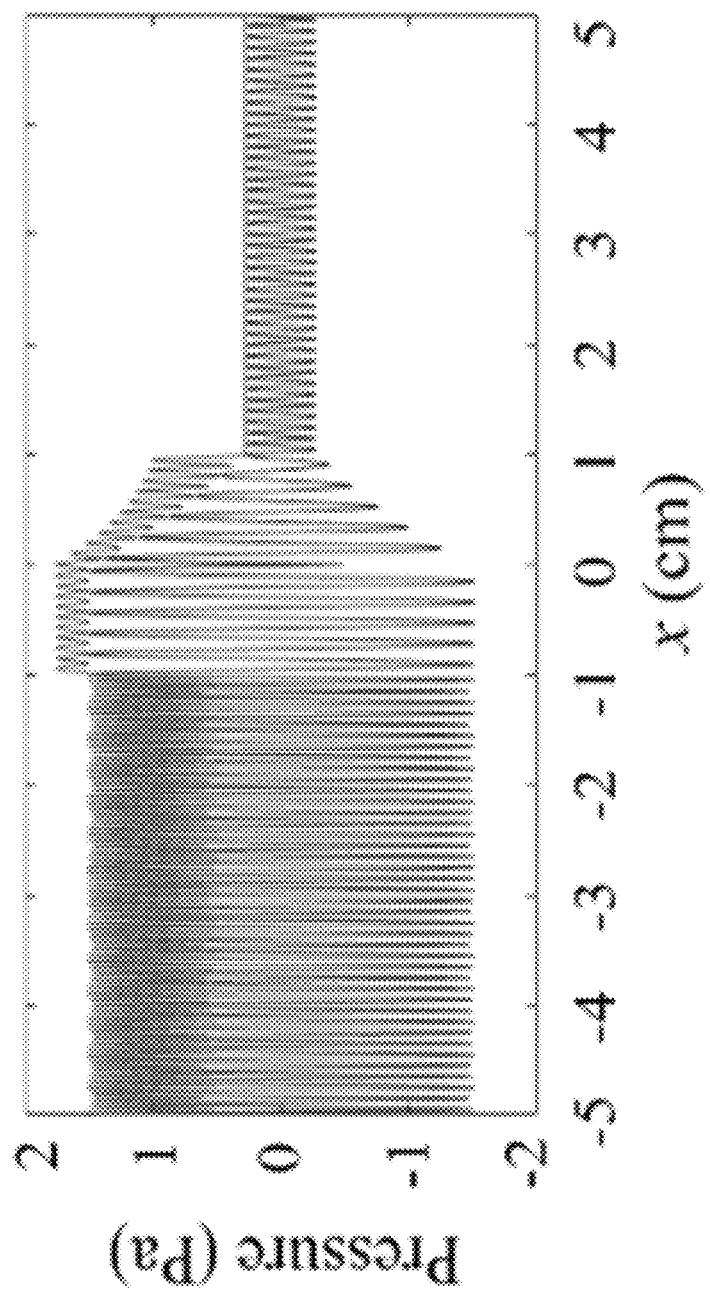
Figure 4D:
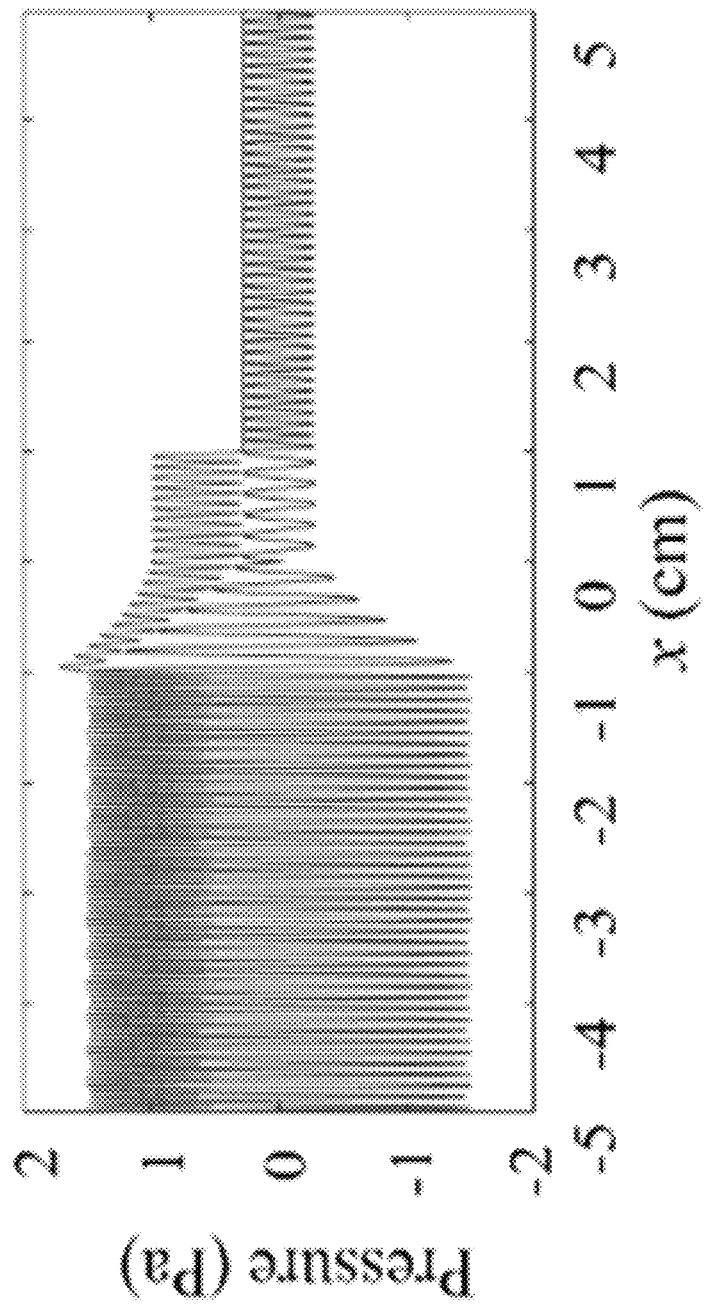
Figure 4E:
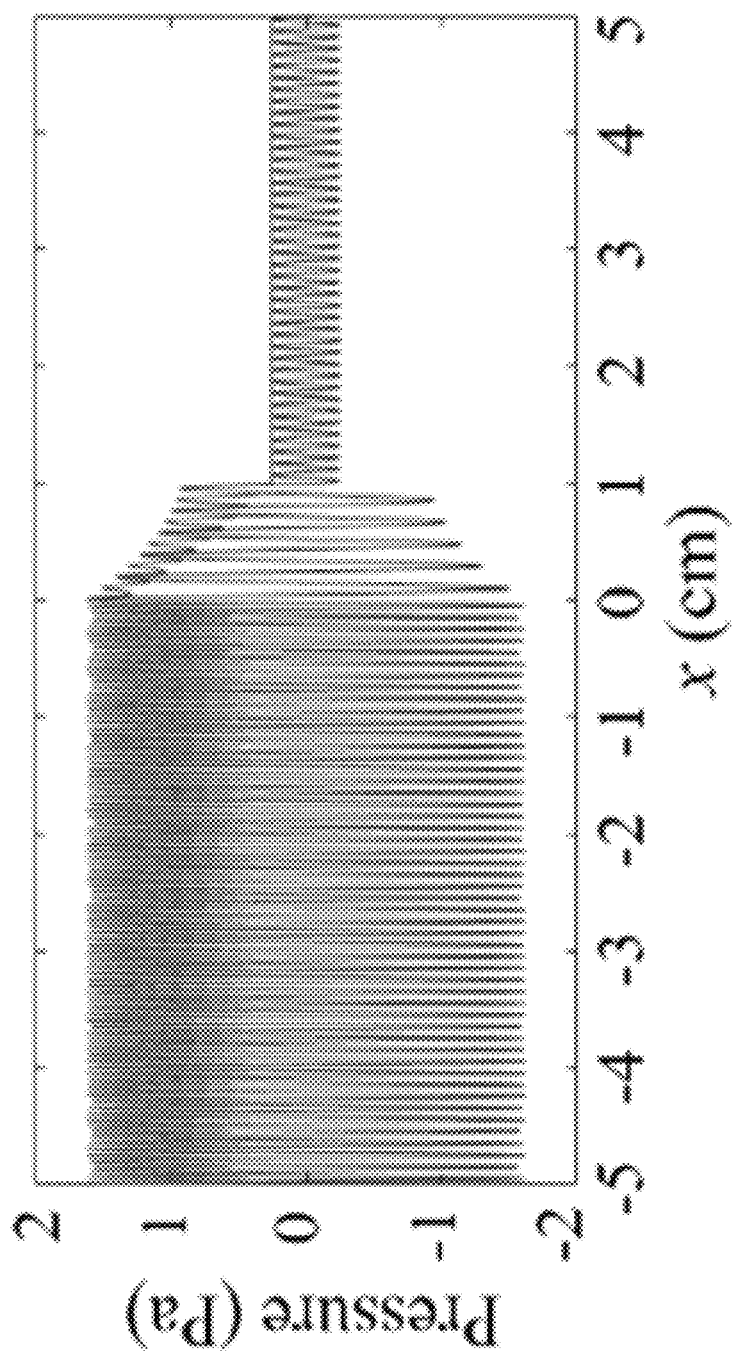

For comparison, the acoustic transmission and reflection from the skull compensated by a complementary metamaterial (CMM) are also calculated (FIGS. 4C and 4D) with the transmitted acoustic energy reducing to 35% of the incident (12% in terms of energy), and a strong reflection is observed for incidence from either side. Without wishing to be bound by any one scientific theory, it is evident that the real part of the skull impedance is affected by the imaginary parts of the material parameters. The mismatched impedance induces an acoustic reflection boundary and acoustic energy loss make the CMM ineffective, and insignificantly beneficial compared to the energy transmission direction through the skull (FIG. 4E).

Figure 5A:
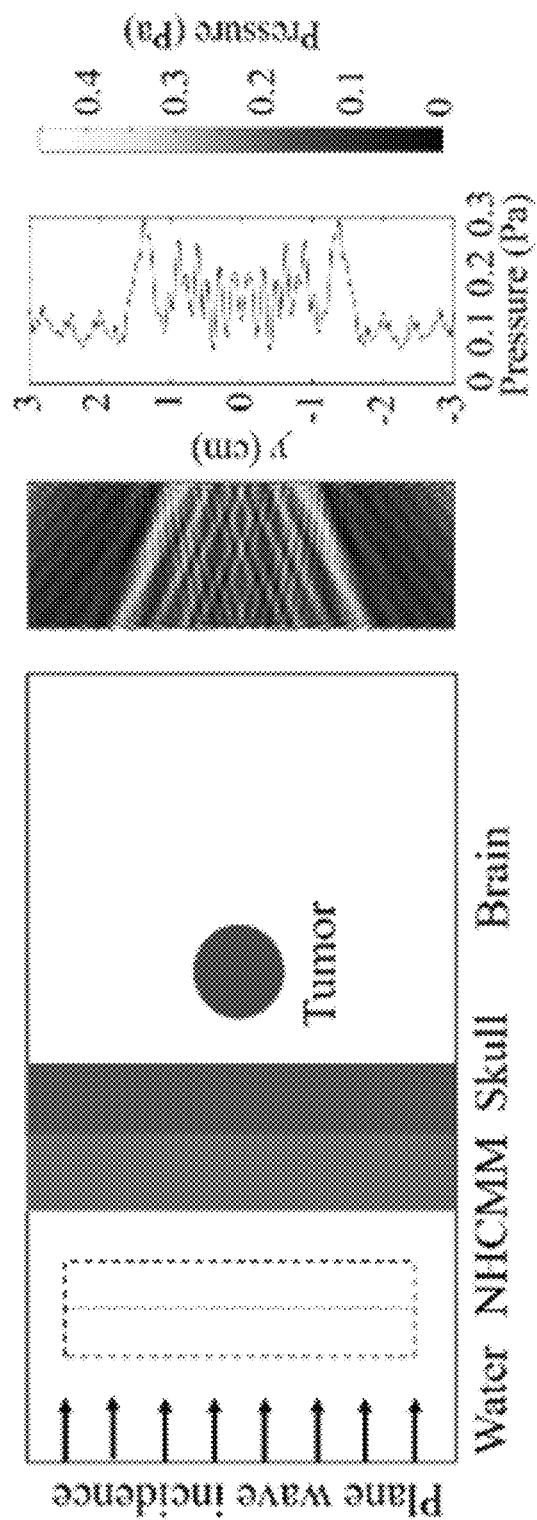
FIGS. 5A-D illustrate acoustic imaging through the tissue of a specimen compensated by various materials according to some examples of the present disclosure.
Figure 5B:
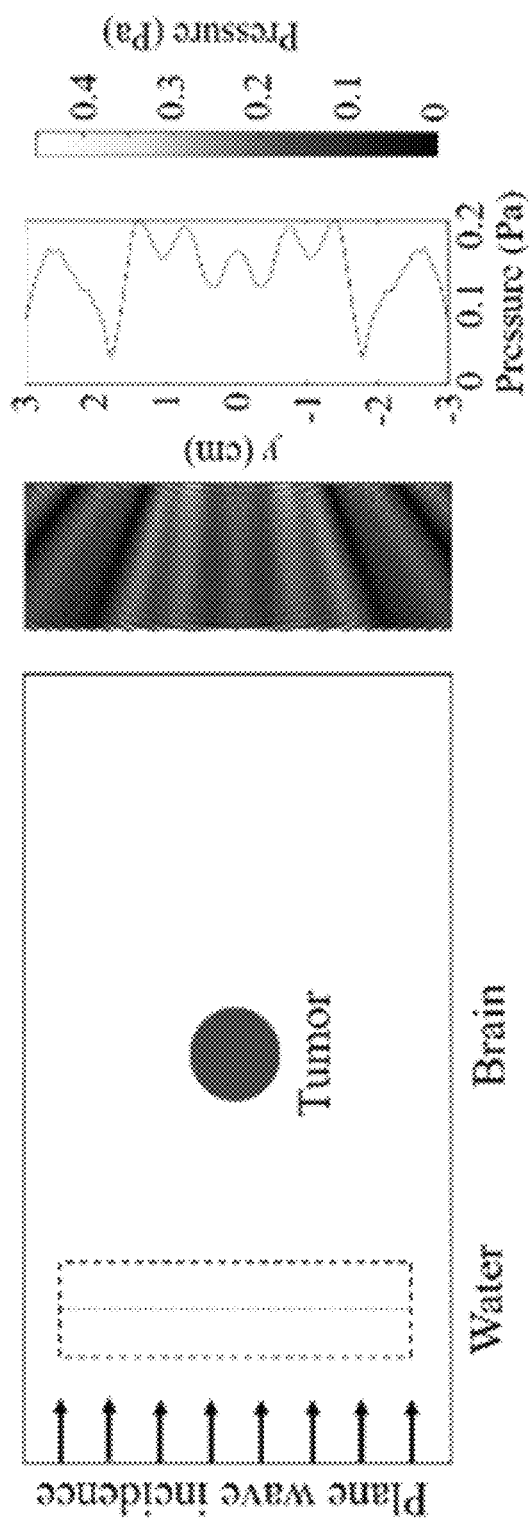
Figure 5C:
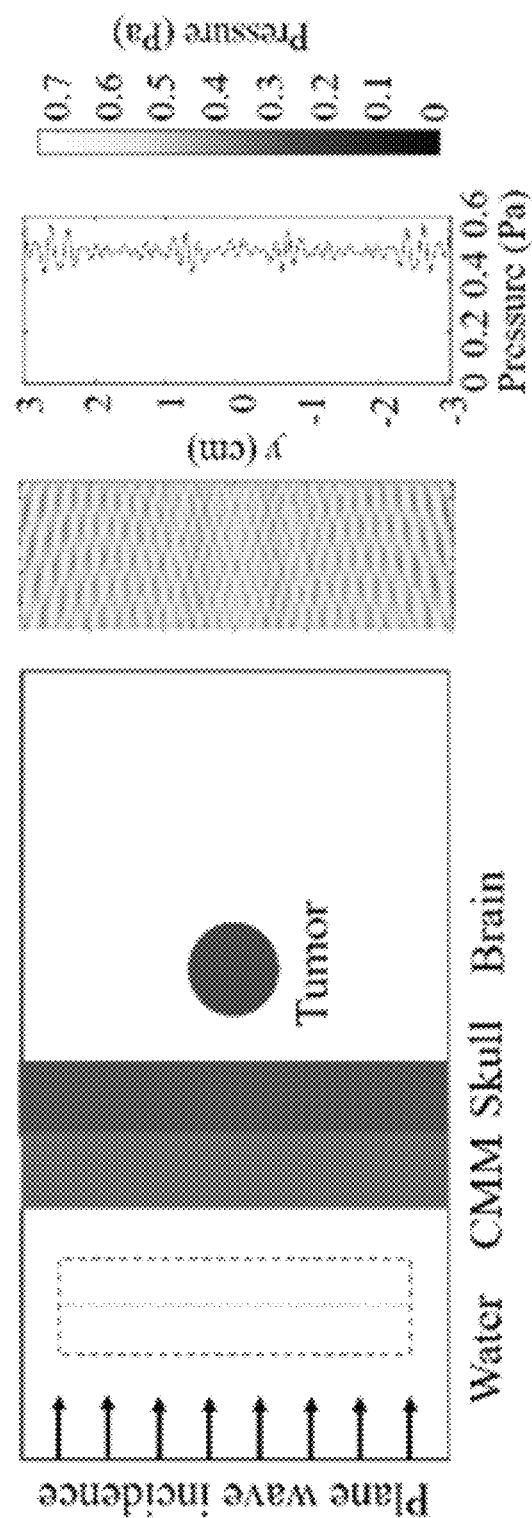
Figure 5D:
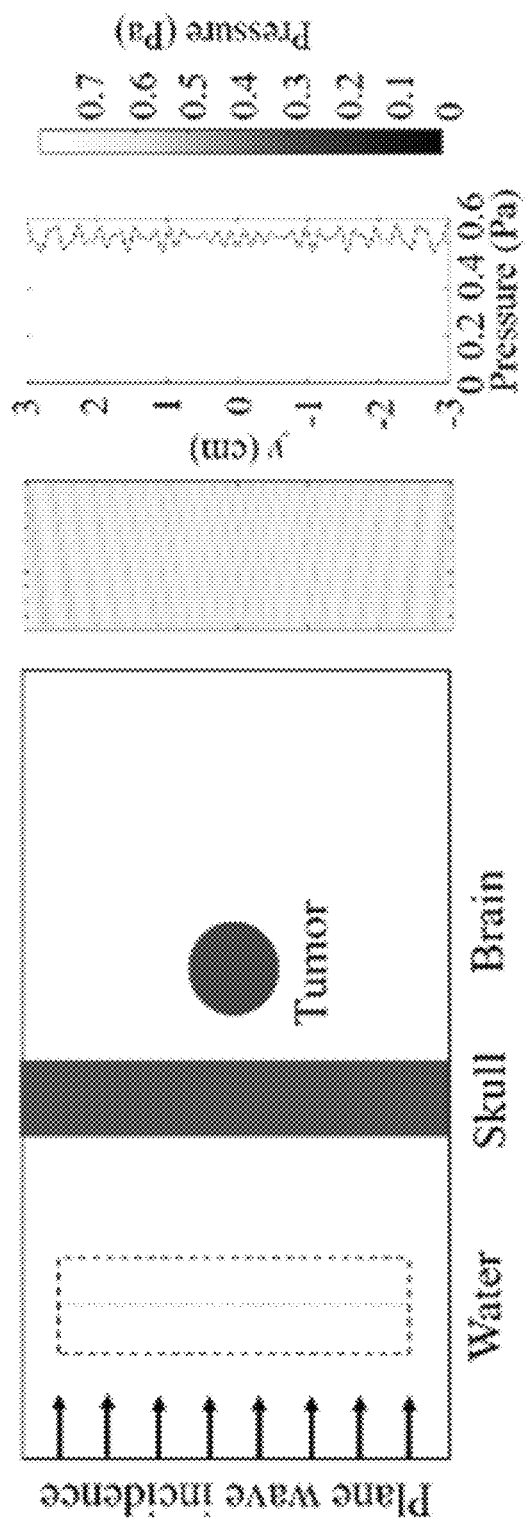

The ultrasonic imaging performance can be characterized by calculating the scattered acoustic field from a brain tumor through the skull complemented by the NHCMM (FIG. 5A). The brain tumor can be modeled by a circle with a 2-cm diameter located 2 cm away from the inner boundary of the skull. The density and sound speed of the brain tumor can be set to be $\rho_t=1500$ kg/m$^3$ and $c_t=2000$ m/s. For comparison, the scattered field from the same brain tumor without transmitting through the bilayer structure is calculated (FIG. 5B). In this case, the field under analysis can be 2 cm closer to the tumor than the case where the skull is compensated by the NHCMM due to the lack of phase accumulation across the bilayer (FIGS. 4A and 4B). In both cases, the shadow lines of the brain tumor can be observed in the reflected pressure amplitude fields. The pressure amplitude of the reflected wave along a line 2 cm away from the outer boundary of the NHCMM for both cases can be plotted. The shadows can be located at y=±1.8 cm for both cases, indicating the existence of the circular brain tumor. These shadows can demonstrate the effectiveness of the NHCMM. On the other hand, when the real-part based CMM is used, most of the acoustic energy is reflected back from the bilayer and no shadow of the brain tumor is found (FIG. 5C), similar to directly imaging through the lossy skull layer (FIG. 5D). Thus, the brain tumor cannot be detected by ultrasound through the skull complemented by the CMM.

Figure 6A:
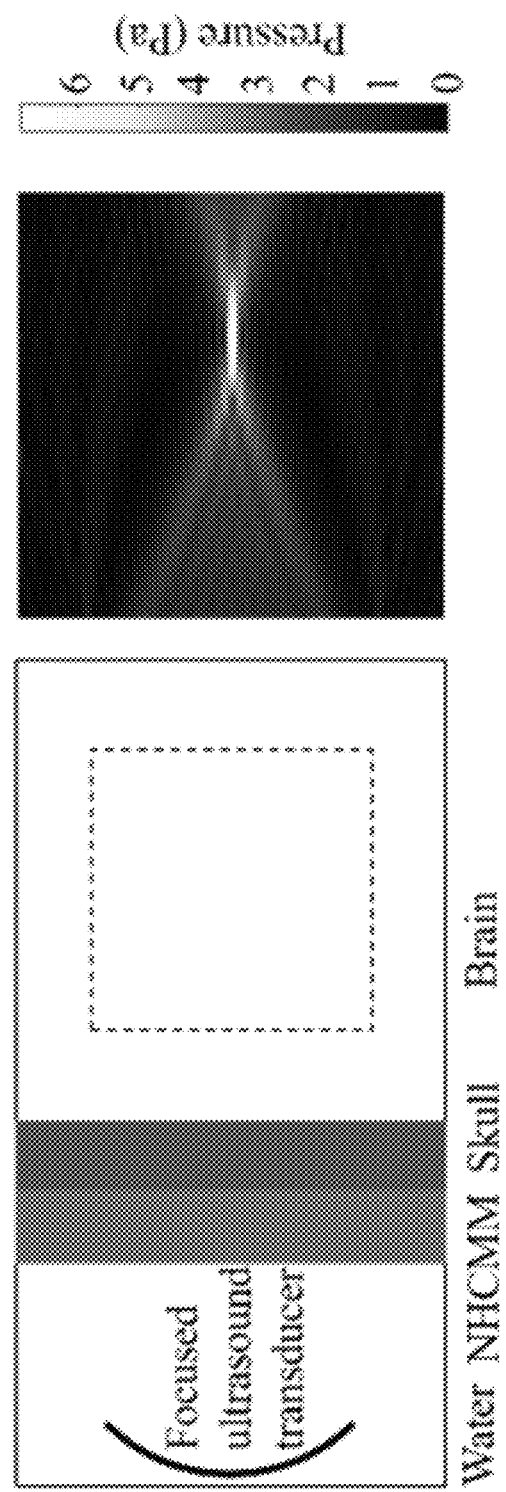
FIGS. 6A-D illustrate an acoustic imaging system focused through a tissue according to some examples of the present disclosure.
Figure 6B:
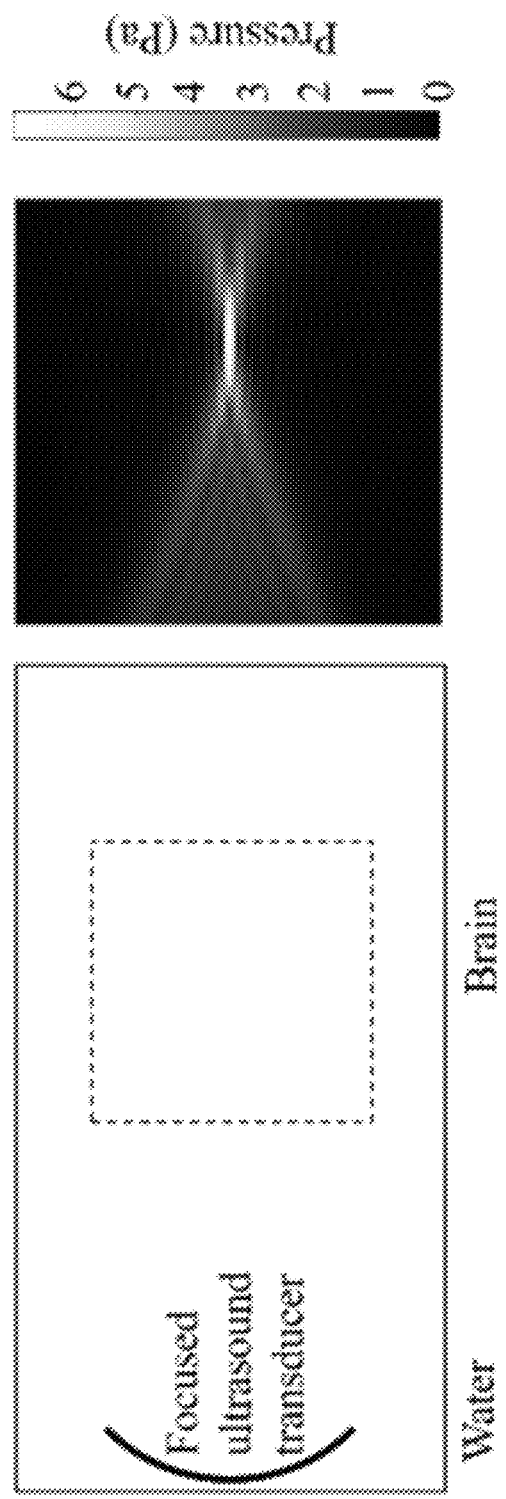
Figure 6C:
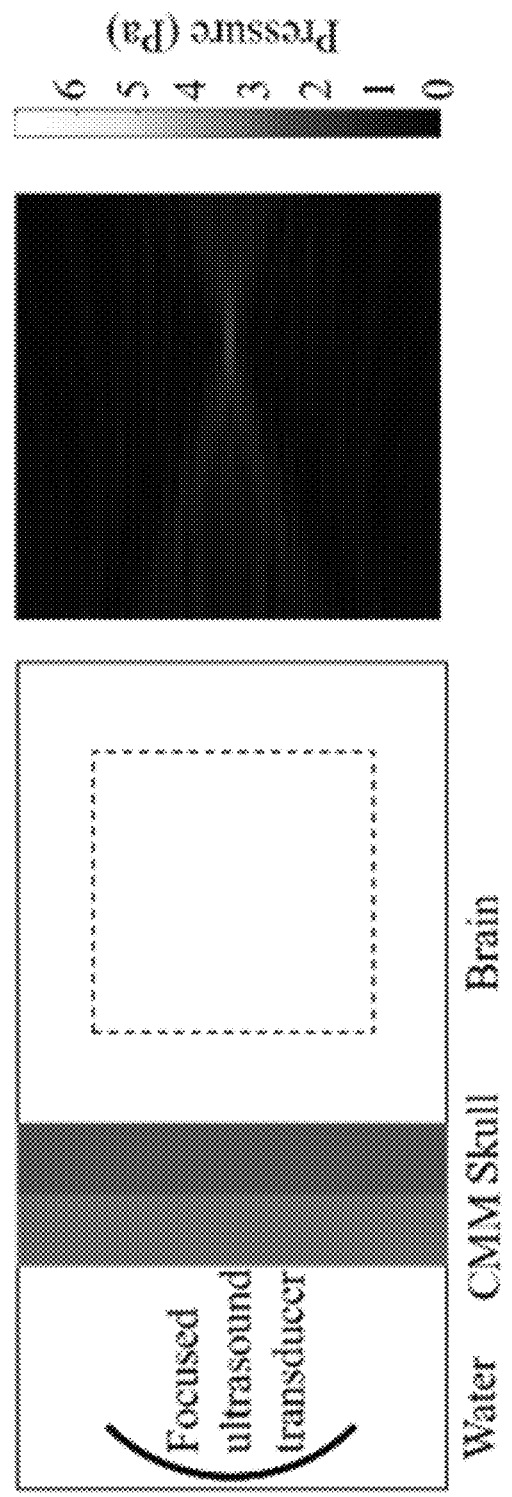
Figure 6D:
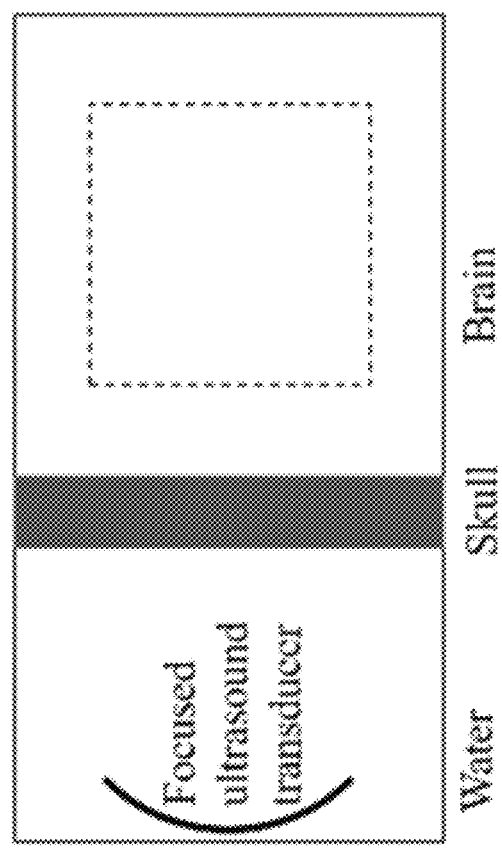

Another widely used type of acoustic wave in biomedical applications like neuron stimulations, ablation, thalamotomy, and drug delivery is focused ultrasound. The propagation of waves generated by a curved focused ultrasound transducer through the skull complemented by the NHCMM compared with the focused wave without the skull are also calculated (FIGS. 6A and 6B). The two cases have a similar focusing effect with almost the same amount of energy concentrated at the focal point. When the skull is complemented by the CMM, the acoustic energy has the same focal point, but at a much lower energy level (FIG. 6C). Without wishing to be bound by any particular scientific theory, this can be because the refractive index of a medium can be determined by the real part of the sound speed. With the same real part of the sound speed, the refractive index of the CMM can be identical to that of the NHCMM, resulting in the same wave refraction and focusing effect. However, the CMM does not compensate the lossy skull, resulting in a much lower focal energy. For the case without any complementary layer, the ultrasound through the skull directly focuses at a point approximately 3 cm to the left compared with the other cases (FIG. 6D). This is because the skull has a different refractive index compared with the water and brain, and the resulted wave refraction changes the location of the focal point. The focused acoustic energy is also low because most of the acoustic waves are reflected or damped by the skull.

What is claimed is:

1. An acoustic transmission system comprising:
    an acoustic wave generator configured to generate an acoustic wave and propagate the acoustic wave through a lossy tissue of a specimen; and
    a non-Hermitian complementary metamaterial (NHCMM) configured to add a first amount of energy amplification coherently to the acoustic wave to account for energy loss in the acoustic wave as a result of the wave propagating through the tissue of the specimens;
    wherein active gain elements in the NHCMM compensate the acoustic wave attenuation through the lossy tissue.

2. The acoustic transmission system of claim 1, wherein the NHCMM has a first bulk modulus and a first density having an opposite sign to a second bulk modulus and a second density of the tissue, respectively.

3. The acoustic transmission system of claim 1, wherein the acoustic wave generator is an ultrasound generator.

4. The acoustic transmission system of claim 2 further comprising:
    a processor; and
    a memory storing instructions that, when executed by the processor, cause the system to:
        transmit a first acoustic wave from the acoustic wave generator through the tissue to determine the second bulk modulus and the second density;
        calculate an impedance mismatch and an intrinsic loss of the tissue;
        alter the NHCMM to coherently amplify the first amount of energy to compensate for the impedance mismatch and the intrinsic loss; and
        transmit a second acoustic wave from the acoustic wave generator through the tissue.

5. The acoustic transmission system of claim 4 further comprising a transducer;
    wherein the instructions further cause the system to:
        measure a pressure field of the tissue with the transducer;
        calculate a contrast to noise ratio of the pressure field; and
        determine if an anomaly is present in the pressure field by comparing the measured
        pressure field to a higher amplitude backscattered pressure field.

6. An acoustic transmission system comprising:
    an acoustic wave generator configured to generate an acoustic wave and propagate the acoustic wave through a lossy tissue of a specimen; and
    a non-Hermitian complementary metamaterial (NHCMM) configured to add a first amount of energy amplification coherently to the acoustic wave to account for energy loss in the acoustic wave as a result of the wave propagating through the tissue of the specimen;
    wherein negative real parts of the NHCMM are realized by resonating structures, while imaginary parts are contributed by the active gain elements.

7. The acoustic transmission system of claim 1, wherein the NHCMM is positioned proximal to the tissue.

8. A method of acoustic wave transmission using the system of claim 2 comprising:

transmitting a first acoustic wave from the acoustic wave generator to propagate the first acoustic wave through the tissue to determine the first bulk modulus and the first density of the tissue;
calculating an impedance mismatch and an intrinsic loss of the tissue;
forming a second acoustic wave by altering the non-Hermitian complementary metamaterial (NHCMM) to:
have the second bulk modulus and the second density; and
add the first amount of energy to the first acoustic wave to compensate for the impedance mismatch and the intrinsic loss; and
transmitting the second acoustic wave from the acoustic wave generator into the tissue, wherein the NHCMM is positioned proximal to the tissue.

9. The method of claim 8 further comprising:
measuring a pressure field produced by the second acoustic wave propagating through the tissue by a transducer;
calculating a contrast to noise ratio of the pressure field; and
determining if an anomaly is present in the pressure field by comparing the measured pressure field to a higher amplitude backscattered pressure field.

10. The method of claim 8, wherein the tissue is a cranium.

11. The method of claim 8, wherein the acoustic wave generator is an ultrasound generator.

12. The acoustic transmission system of claim 1 further comprising:
a processor; and
a memory storing instructions that, when executed by the processor, cause the system to:
transmit a first acoustic wave from the acoustic wave generator to propagate the first acoustic wave through the tissue of the specimen to determine a first bulk modulus and a first density of the tissue;
calculate an energy loss in the first acoustic wave as a result of the first acoustic wave propagating through the tissue;
alter the non-Hermitian complementary metamaterial (NHCMM) to coherently amplify the first amount of energy to the acoustic wave generator to compensate the energy loss in the first acoustic wave to form a second acoustic wave; and
transmit the second acoustic wave from the acoustic wave generator into the tissue, wherein the NHCMM is positioned proximal to and the tissue.

13. The acoustic transmission system of claim 12 further comprising a transducer;
wherein the instructions further cause the system to:
measure a pressure field produced by the second acoustic wave propagating through the tissue by the transducer;
calculate the contrast to noise ratio of the pressure field; and
determine if an anomaly is present in the pressure field by comparing the measured pressure field to a higher amplitude backscattered pressure field.

14. The acoustic transmission system of claim 12, wherein the tissue is a cranium.

15. The acoustic transmission system of claim 12, wherein the acoustic wave generator is an ultrasound generator.

16. The acoustic transmission system of claim 12, wherein the NHCMM comprises a resonating structure.

17. The acoustic transmission system of claim 6, wherein the NHCMM is in electrical communication with an electronic circuit.

18. The acoustic transmission system of claim 17, wherein the electronic circuit comprises piezoelectric materials connected to an amplification and a phase control circuit.

* * * * *